(12) United States Patent
Ward et al.

(10) Patent No.: US 7,879,304 B1
(45) Date of Patent: Feb. 1, 2011

(54) MONODISPERSE MESOPOROUS SILICA MICROSPHERES FORMED BY EVAPORATION-INDUCED SELF-ASSEMBLY OF SURFACTANT TEMPLATES IN AEROSOLES

(75) Inventors: Timothy L Ward, Albuquerque, NM (US); Jaime Bravo, Albuquerque, NM (US); Abhaya Datye, Albuquerque, NM (US); Gabriel Lopez, Albuquerque, NM (US); Hien Pham, Albuquerque, NM (US); Shailendra Rathod, Albuquerque, NM (US); Venkata Goparaju, Albuquerque, NM (US)

(73) Assignee: STC. UNM, Albusquerque, NM (US)

( * ) Notice: Subject to any disclaimer, the term of this patent is extended or adjusted under 35 U.S.C. 154(b) by 58 days.

(21) Appl. No.: 12/015,412

(22) Filed: Jan. 16, 2008

Related U.S. Application Data

(62) Division of application No. 10/640,249, filed on Aug. 14, 2003, now abandoned.

(60) Provisional application No. 60/410,830, filed on Sep. 16, 2002.

(51) Int. Cl.
*C01B 33/12* (2006.01)

(52) U.S. Cl. ............... 423/336; 423/324; 423/325; 423/326; 423/335

(58) Field of Classification Search ............... 423/324, 423/325, 326, 335, 336
See application file for complete search history.

(56) References Cited

U.S. PATENT DOCUMENTS

| 4,794,086 | A  | * | 12/1988 | Kasper et al. | 436/36 |
| 5,601,235 | A  | * | 2/1997  | Booker et al. | 239/4 |
| 5,922,299 | A  | * | 7/1999  | Bruinsma et al. | 423/335 |
| 6,174,512 | B1 | * | 1/2001  | Kosuge et al. | 423/705 |
| 6,299,855 | B1 | * | 10/2001 | Lujano et al. | 423/702 |
| 6,387,453 | B1 | * | 5/2002  | Brinker et al. | 427/387 |
| 7,052,665 | B2 | * | 5/2006  | Fortier et al. | 423/328.1 |

OTHER PUBLICATIONS

Provision U.S. Appl. No. 60/330,847 (Priority for US 7052665).*
Lu et al. "Aerosol-assited self-assembly of mesotructured spherical nanoparticles.", Nature, 1999.*
Rathod, et al. "Monodisperse Mesoporous Microparticles Prepared by Evaporation-Induced Self Assembly Within Aeorosols." Mat. Res. Soc. Symp. Proc. vol. 775, 2003.*
Index of Proceedings of Materials Research Society Symposium Proceedings for Spring 2003 (Including vol. 775).*

* cited by examiner

*Primary Examiner*—Steven Bos
*Assistant Examiner*—Paul A Wartalowicz
(74) *Attorney, Agent, or Firm*—Gonzales Patent Services; Ellen M. Gonzales

(57) ABSTRACT

The present invention provides for evaporation induced self-assembly (EISA) within microdroplets produced by a vibrating orifice aerosol generator (VOAG) for the production of monodisperse mesoporous silica particles. The process of the present invention exploits the concentration of evaporating droplets to induce the organization of various amphiphilic molecules, effectively partitioning a silica precursor to the hydrophilic regions of the structure. Promotion of silica condensation, followed by removal of the surfactant, provides ordered spherical mesoporous particles.

23 Claims, 8 Drawing Sheets

MONODISPERSE MESOPOROUS SILICA MICROSPHERES FORMED BY EVAPORATION-INDUCED SELF-ASSEMBLY OF SURFACTANT TEMPLATES IN AEROSOLES

CROSS-REFERENCE TO RELATED APPLICATIONS

This application is a divisional of U.S. patent application Ser. No. 10/640,249, filed Aug. 14, 2003, which claims priority to U.S. Provisional Patent Application No. 60/410,830, filed Sep. 16, 2002, both of which are entitled "Monodisperse Mesoporous Silica Microspheres Formed by Evaporation-Induced Self-Assembly of Surfactant Templates in Aerosols". The entire disclosure and contents of the above applications are hereby incorporated by reference.

GOVERNMENT INTEREST STATEMENT

This invention is made with government support under grant number 318652, awarded by the Air Force Office of Scientific Research and grant numbers 9812899 and 0210835, awarded by the National Science Foundation. The U.S. Government has certain rights in this invention.

BACKGROUND OF THE INVENTION

1. Field of the Invention

The present invention relates generally to monodisperse mesoporous silica microspheres, and more particularly to a method of forming monodisperse mesoporous silica microspheres by evaporation-induced self-assembly of surfactant templates in aerosols.

2. Description of the Prior Art

Figure 6A:
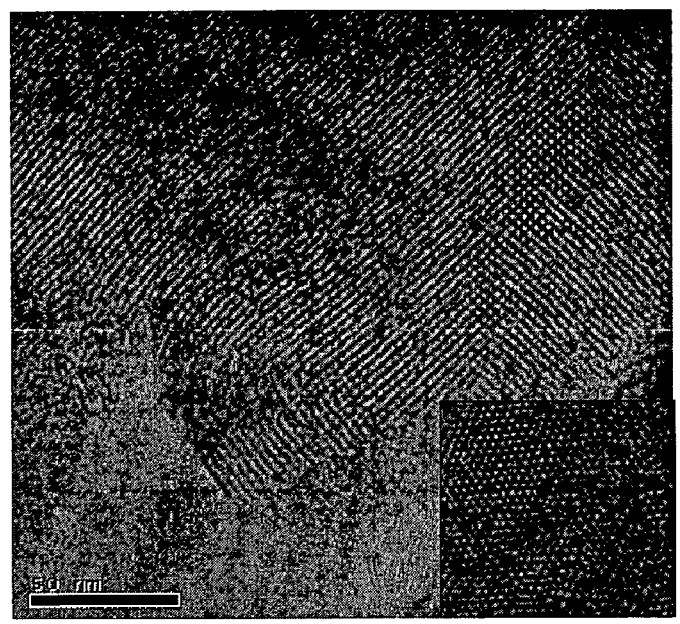
Figure 6B:
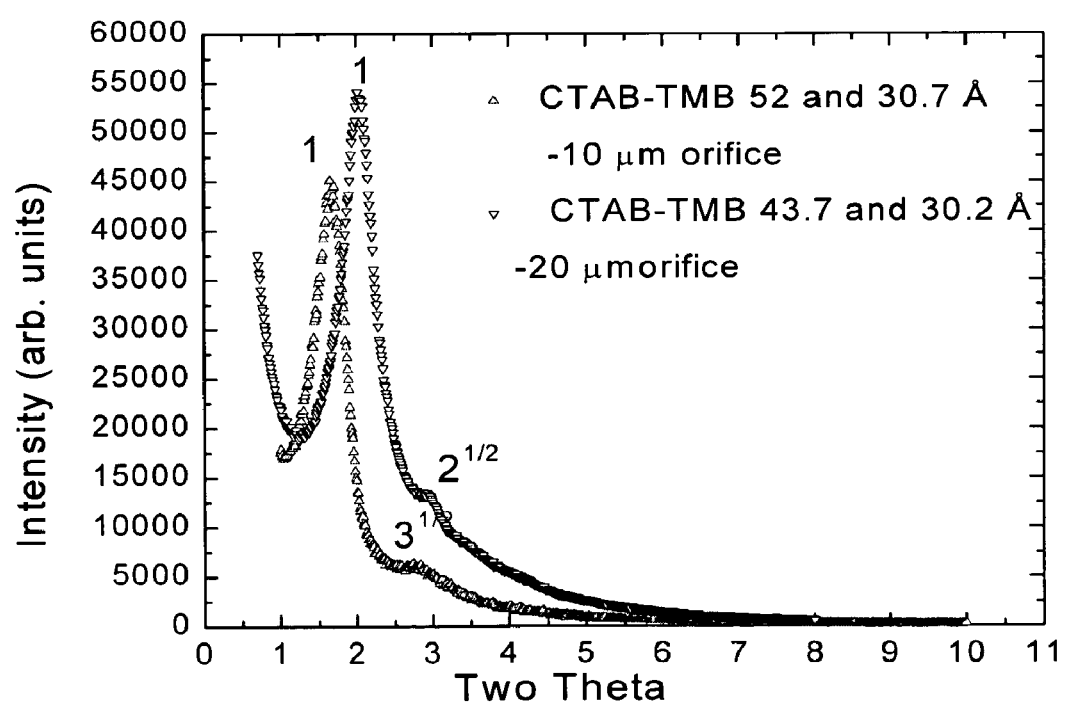
Figure 7:
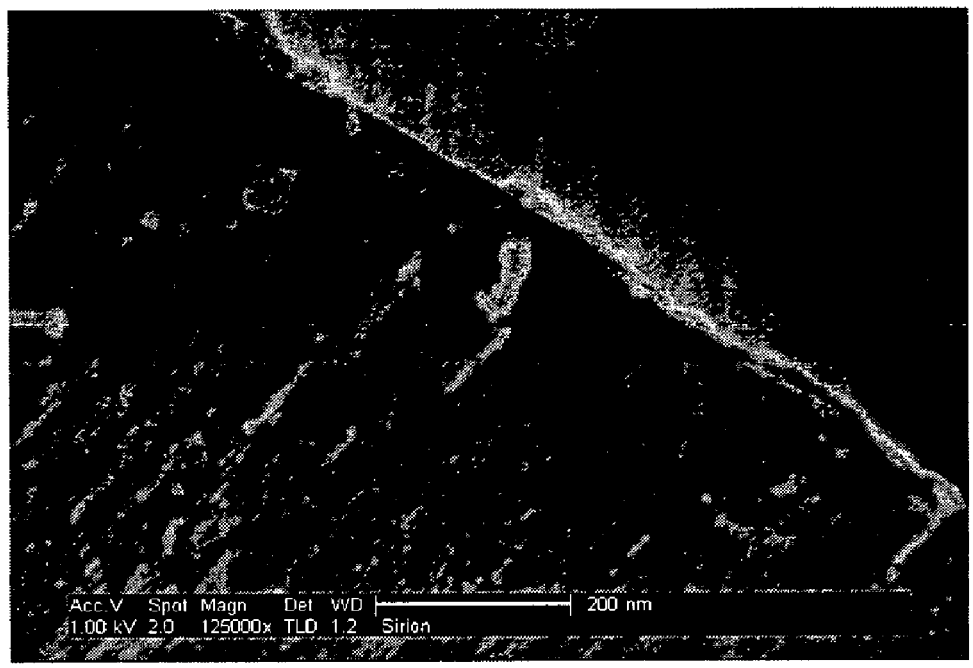
Figure 8:
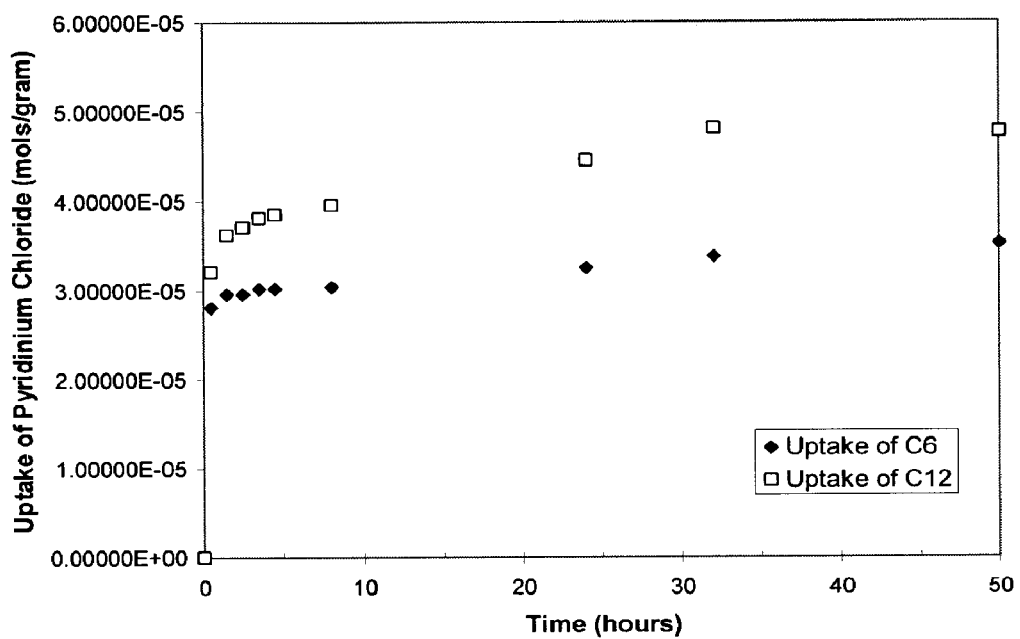

Evaporation-induced self-assembly (EISA) of amphiphilic molecules (e.g., surfactants and block copolymers) within aerosols and thin films has been recently demonstrated to be a powerful and flexible method for synthesizing ordered mesoporous silica particles and thin films, see Y. Lu, H. Fan, A. Stump, T. L. Ward, T. Reiker, C. J. Brinker, Nature, 1999, 398, 223; C. J. Brinker, Y. Lu, A. Sellinger, H. Fan, Adv. Mater., 1999, 11, 579; and Y. Lu, R. Ganguli, C. A. Drewien, M. T. Anderson, C. J. Brinker, W. L. Gong, Y. X. Guo, H. S oyez, B. Dunn, M. H. Huang, J. I. Zink, Nature, 1997, 389, 364, the entire contents and disclosures of which are hereby incorporated by reference. The previous synthesis of mesoporous silica particles using aerosol EISA has been limited to particle sizes of roughly 1 μm or smaller possessing a relatively wide particle size distribution. There are many applications where larger mesoporous particles with high monodispersity are needed or would be highly beneficial. Several examples include: controlled delivery, where monodispersity may ensure uniform delivery rates; biosensing based on flow cytometry, where monodisperse spheres with sizes of several μm could serve as ‘cell mimics’; and photonic bandgap materials, where high monodispersity, periodicity and control of dielectric constant are critical factors, see T. Buranda, G. M. Jones, J. P. Nolan, J. Keij, G. P. Lopez, L. A. Sklar, J. of Phys. Chem. B, 1999, 103, 3399; and J. D. Joannopoulos, P. R. Villeneuve, S. Fan, Nature, 1997, 386, 143, the entire contents and disclosures of which are hereby incorporated by reference. Thus, there is still a need to provide a mechanism for producing such large mesoporous particles.

SUMMARY OF THE INVENTION

It is therefore an object of the present invention to provide a mechanism for producing large mesoporous particles.

It is a further object to provide a method of forming monodisperse mesoporous silica microspheres by evaporation-induced self-assembly of surfactant templates in aerosols.

According to a first broad aspect of the present invention, there is provided a method of producing monodisperse mesoporous silica spheres comprising combining a precursor aqueous or alcohol based solution comprising tetraethylorthosilicate with an amphiphile to form a sol, creating monodisperse droplets of the sol using a vibrating orifice aerosol generator, evaporating solvent from the monodisperse droplets of the sol to induce self-assembly of the amphiphile in the monodisperse spheres, heating to promote condensation of the tetraethylorthosilicate to produce the silica, and removal of the amphiphile by thermal or chemical means.

According to second broad aspect of the invention, there is provided monodisperse mesoporous silica spheres comprising a plurality of pores derived from an amphiphile template in a precursor aqueous or alcohol based solution comprising tetraethylorthosilicate and the amphiphile, wherein the monodisperse mesoporous silica spheres are formed by creating monodisperse droplets of the solution using a vibrating orifice aerosol generator, evaporating solvent from the monodisperse droplets of the solution, heating the spheres to promote condensation of the tetraethylorthosilicate to form silica, and removal of the amphiphile by thermal or chemical means.

Other objects and features of the present invention will be apparent from the following detailed description of the preferred embodiment.

BRIEF DESCRIPTION OF THE DRAWINGS

The invention will be described in conjunction with the accompanying drawings, in which:

FIGS. 1A and 1B are scanning electron micrographs of porous silica particles obtained using: (FIG. 1A) A2 sol, CTAB surfactant and a 20 μm VOAG orifice, and (FIG. 1B) A2 sol, Brij-58 surfactant and a 10 μm VOAG orifice;

FIG. 2 shows X-ray diffraction patterns of mesoporous silica particles prepared using CTAB (a) and Brij-58 (b);

FIGS. 3A and 3B show transmission electron microscopy (TEM) images obtained from ultra-microtomed sections of mesoporous particles produced with an A2 sol and surfactants CTAB (FIG. 3A) and Brij-58 (FIG. 3**B);

FIGS. 4A and 4B show TEM images obtained from ultra-microtomed sections of a particle produced using the aqueous TEOS precursor solution with CTAB surfactant: (FIG. 4A) a region where pores are apparently aligned parallel to the particle surface, and (FIG. 4B) a region showing some pore channels aligned perpendicular to the particle surface;

FIGS. 5A and 5B show X-ray diffraction patterns on mesoporous silica powders produced using CTAB with and without addition of swelling agent trimethylbenzene (TMB) (FIG. 5A), and produced using block copolymer F-127 as an amphiphile (FIG. 5B), with pore size and surface area also shown from $N_2$ adsorption measurements;

FIGS. 6A and 6B show a TEM image and an X-ray diffraction pattern for fractured particles produced using a 20 micrometer VOAG orifice with a CTAB/A2** sol containing trimethylbenzene as a phase modifying agent; with an inset in FIG. 6A showing an alternate orientation from another region at the same magnification, and data using the same formulation with a 10 micrometer VOAG orifice shown in FIG. 6B, with d-spacings of the two strongest peaks noted in the legend;

FIG. 7 is a scanning electron micrograph showing a fracture surface of a mesoporous particle produced using block copolymer F-127 as an amphiphile; and FIG. 8 shows uptake of hexyl and decyl pyridinium chloride (C6 and C12, respectively) from aqueous solutions by mesoporous silica particles produced using a F127 amphiphile.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "monodisperse" refers to a state or system in which all or substantially all the particles are of approximately the same size.

For the purposes of the present invention, the term "mesoporous" refers to a material having at least one pore with a diameter between 1.5 and 50 nm in at least one direction.

For the purposes of the present invention, the term "evaporation-induced self-assembly" refers to the evaporation of molecules (typically a solvent), which, due to the concentration of amphiphiles, induces spontaneous self-organization of said amphiphiles to produce one or more mesophases.

For the purposes of the present invention, the term "amphiphile" refers to a molecule with both solvent-phobic and solvent-philic ends.

For the purposes of the present invention, the term "vibrating orifice aerosol generator (VOAG)" refers to a device that generates uniform particles by controlling the breakup of a liquid jet. A VOAG is a highly accurate source of monodisperse particles in the range from about 1 to about 200 micrometers.

For the purposes of the present invention, the term "swelling agent" refers to an agent that preferentially locates into one region of micellar or liquid crystalline structures, effectively leading to an increase in the size of those structural regions. An exemplary swelling agent of the present invention is trimethylbenzene.

For the purposes of the present invention, the term "block copolymer" refers to a polymer in which all of one type of monomer are grouped together, and all of at least one other monomer are grouped together. An exemplary block copolymer of the present invention is F127 ((ethylene oxide)$_{106}$ (propylene oxide)$_{70}$(ethylene oxide)$_{106}$).

For the purposes of the present invention, the term "diameter" refers to the distance from one side to an opposite side of an object, such as a pore, particle, etc. in any direction through the middle of the object. The maximum diameter of an object is the longest diameter for that object.

For the purposes of the present invention, the term "non-hollow" refers to a particle that is not hollow, where "hollow" is meant to indicate a particle that possesses an interior void that is roughly centrally located and has a diameter greater than roughly one fourth of the particle diameter.

For the purposes of the present invention, the term "aerosol" refers to a droplet possessing a diameter less than approximately 100 micrometer.

For the purposes of the present invention, the term "influences mesophase behavior" refers to the function of an agent as a phase modifying agent that facilitates the formation of a more complex phase than would be formed without the agent.

For the purposes of the present invention, the term "removal of an amphiphile by thermal or chemical means" refers to any suitable chemical or thermal means for removal of an amphiphile, such as, but not limited to, calcination in a gaseous environment at sufficiently high temperature to volatilize or combust the organic, use of a solvent to displace, dissolve or remove the organic, etc.

DESCRIPTION

The present invention provides a means to produce monodisperse mesoporous silica spheres by exploiting evaporation-induced self-assembly of amphiphilic molecules in monodisperse droplet streams produced by a vibrating orifice aerosol generator. This type of droplet generator is commercially available and relies on piezoelectric disruption of a fluid stream to produce the monodisperse droplets. Using aqueous or alcohol based solutions containing the silica precursor tetraethylorthosilicate (TEOS), monodisperse ordered mesoporous particles have been reproducibly produced from four exemplary precursor systems. First, utilizing the cationic surfactant cetyl trimethyl ammonium bromide in acidic pre-hydrolyzed solutions of TEOS, monodisperse spherical particles may be produced that possess hexagonally ordered pores with mean pore diameters of approximately 1.8 nm. Second, utilizing the nonionic surfactant Brij-58 in acidic pre-hydrolyzed solutions of TEOS, monodisperse spherical particles may be produced that possess hexagonally ordered pores with pore diameters of approximately 2.8 nm. Third, utilizing the block copolymer F-127 as a templating agent in acidic pre-hydrolyzed solutions of TEOS, monodisperse spherical particles may be produced that possess hexagonally ordered pores with pore diameters of approximately 6.9 nm. Fourth, utilizing the cationic surfactant cetyl trimethyl ammonium bromide with roughly equimolar trimethylbenzene in acidic pre-hydrolyzed solutions of TEOS with the VOAG 20 μm diameter orifice, monodisperse spherical particles may be produced that possess cubically ordered pores with a mean pore diameter of approximately 2.2 nm. In a preferred embodiment, particle diameters in the 3-10 μm range may be produced by the present invention.

However, particle sizes up to 50 μm may be produced by the methods of the present invention for all precursor systems. In addition, pore sizes may be controlled over the range of 2-10 nm by choice of surfactant and/or use of swelling additives.

The present invention provides for the synthesis of non-hollow monodisperse mesoporous silica particles, typically in the 3 to 10 μm size range, based on evaporation-driven surfactant templating in microdroplets produced by a vibrating orifice aerosol generator (VOAG). The present invention shows that pore size, mesoscopic ordering, and monodisperse particle size may be controlled by the experimental conditions, precursor chemistry, and VOAG parameters. The present invention provides for the use of evaporation-driven concentration of solutions as a means to drive the self-assembly process in thin films and small (micron to submicron) droplets, see also Y. Lu, R. Ganguli, C. A. Drewien, M. T.

Anderson, C. J. Brinker, W. L. Gong, Y. X. Guo, H. Soyez, B. Dunn, M. H. Huang, and J. I. Zink, Nature, 389, 364 (1997); C. J. Brinker, Y. Lu, A. Sellinger, and H. Fan, Adv. Mater., 11 (7), 579-585 (1999); Y. Lu, H. Fan, A. Stump, T. L. Ward, T. Reiker, C. J. Brinker, Nature, 398, 223 (1999); and M. T. Bore, S. B. Rathod, T. L. Ward, and A. K. Datye, Langmuir, 19 (2), 256-264 (2003); the entire contents and disclosures of which are hereby incorporated by reference. The present invention has also demonstrated that a variety of highly ordered mesostructures in spherical submicron silica particles may be produced using this "evaporation-induced self-assembly" (EISA) process with aerosol droplets, see Y. Lu, H. Fan, A. Stump, T. L. Ward, T. Reiker, C. J. Brinker, Nature, 398, 223 (1999); and M. T. Bore, S. B. Rathod, T. L. Ward, and A. K. Datye, Langmuir, 19 (2), 256-264 (2003); the entire contents and disclosures of which are hereby incorporated by reference.

Surfactant-templated mesoporous materials, initially discovered by Mobil scientists in 1992, have been developed to exhibit unique structures and properties, including uni-modal pore size distributions, high surface areas, alterable pore sizes and controlled pore surface chemistry, see C. Kresge, M. Leonowicz, W. Roth, C. Vartuli, J. Beck, Nature, 1992, 359, 710; and J. S. Beck, J. C. Vartuli, W. J. Roth, M. E. Leonowicz, C. T. Kresge, K. D. Schmitt, C. T. W. Chu, D. H. Olson, E. W. Shephard, S. B. McCullen, J. B. Higgins, J. L. Schlenker, J. Am. Chem. Soc., 1992, 114, 10834, the entire contents and disclosures of which are hereby incorporated by reference. The mesopore size range of 2 to 50 nm is attractive for producing confined structures such as quantum dots or nanowires, see H. Parala, H. Winkler, M. Kolbe, A. Wohlfart, R. A. Fischer, R. Schmechel, J. von Seggern, Adv. Mater., 2000, 12, 1050; V. I. Srdanov, I. Alxneit, G. D. Stucky, C. M. Reaves, S. P. DenBaars, J. Phys. Chem. B, 1998, 102, 3341; T. Hirai, H. Okubo, I. Komasawa, J. Phys. Chem. B, 1999, 103, 4228; Y. J. Han, J. M. Kim, G. D. Stucky, Chem. Mater., 2000, 12, 2068; and M. H. Huang, A. Choudrey, P. D. Yang, Chem. Commun., 2000, 1063, the entire contents and disclosures of which are hereby incorporated by reference. The highly uniform porosity of the mesoporous materials allows for facile diffusion, thereby making them excellent hosts for sensing molecules and ions, see J. Y. Ying, C. P. Mehnert, M. S. Wong, Angew. Chem. Int. Ed., 1999, 38, 56; A. Sayari, S. Hamoudi, Chem. Mater., 2001, 13, 3151; and B. J. Scott, G. Wirnsberger, G. D. Stucky, Chem. Mater., 2001, 13, 3140, the entire contents and disclosures of which are hereby incorporated by reference. The traditional synthetic approach to these materials involves spontaneous self-assembly of amphiphilic molecules from a bulk solution, with concurrent templating of inorganic precursor species through electrostatic or hydrogen bonding interactions with the amphiphilic molecules. This basic approach has led to the synthesis of various mesostructured materials in the form of powders, particles, thin films, and fibers, see C. Kresge, M. Leonowicz, W. Roth, C. Vartuli, J. Beck, Nature, 1992, 359, 710; J. S. Beck, J. C. Vartuli, W. J. Roth, M. E. Leonowicz, C. T. Kresge, K. D. Schmitt, C. T. W. Chu, D. H. Olson, E. W. Shephard, S. B. McCullen, J. B. Higgins, J. L. Schlenker, J. Am. Chem. Soc., 1992, 114, 10834; G. A. Ozin, E. Chomski, D. Khushalani, M. J. Maclachlan, Curr. Opin. Colloid Interface Sci., 1998, 3, 181; S. Sachet, Q. Huo, L. G. Voigt-Martin, G. D. Stucky, F. Schuth, Science, 1996, 273, 768; Q. Huo, J. Feng, F. Schuth, G. D. Stucky, Chem. Mater., 1997, 9, 14; L. Qi, J. Ma, H. Cheng, Z. Zhao, Chem. Mater., 1998, 10, 1623; K. K. Unger, D. Kumar, M. Grun, G. Buchel, S. Ludtke, T. Adam, K. Schumacher, S. Renker, J. Chrom. A, 2000, 892, 47; G. Buchel, M. Grun, K. Unger, A. Mastsumoto, K. Tsutsumi, Supramol. Sci., 1998, 5, 253; K. Kosuge, P. S. Singh, Microporoous Mesoporous Mater., 2001, 44-45, 139; C. E. Fowler, D. Khushalani, S. Maim, Chem. Commun., 2001, 2028; H. Yang, N. Coombs, I. Sokolov, G. Ozin, Nature, 1996, 381, 589; A. Sellinger, P. M. Weiss, A. Nguyen, Y. Lu, R. A. Assink, W. Gong, C. J. Brinker, Nature, 1998, 394, 256; and P. Yang, D. Zhao, B. F. Chmelka, G. D. Stucky, Chem. Mater., 1998, 10, 2033, the entire contents and disclosures of which are hereby incorporated by reference. Mesoporous microspheres have been produced by several different strategies based on the traditional solution synthesis, see S. Sachet, Q. Huo, L. G. Voigt-Martin, G. D. Stucky, F. Schuth, Science, 1996, 273, 768; Q. Huo, J. Feng, F. Schuth, G. D. Stucky, Chem. Mater., 1997, 9, 14; L. Qi, J. Ma, H. Cheng, Z. Zhao, Chem. Mater., 1998, 10, 1623; K. K. Unger, D. Kumar, M. Grun, G. Buchel, S. Ludtke, T. Adam, K. Schumacher, S. Renker, J. Chrom. A, 2000, 892, 47; G. Buchel, M. Grun, K. Unger, A. Mastsumoto, K. Tsutsumi, Supramol. Sci., 1998, 5, 253; K. Kosuge, P. S. Singh, Microporous Mesoporous Mater., 2001, 44-45, 139; and C. E. Fowler, D. Khushalani, S. Mann, Chem. Commun., 2001, 2028, the entire contents and disclosures of which are hereby incorporated by reference. Polydisperse silica spheres ranging in size from submicron to tens of microns have been produced using a 1-alkylamine templating technique, see K. K. Unger, D. Kumar, M. Grun, G. Buchel, S. Ludtke, T. Adam, K. Schumacher, S. Renker, J. Chrom. A, 2000, 892, 47; G. Buchel, M. Grun, K. Unger, A. Mastsumoto, K. Tsutsumi, Supramol. Sci., 1998, 5, 253; and K. Kosuge, P. S. Singh, Microporous Mesoporous Mater., 2001, 44-45, 139, the entire contents and disclosures of which are hereby incorporated by reference. Ordered mesoporous spheres have been produced by interfacial reactions conducted in oil/water emulsions, leading to micron to millimeter-sized particles, see S. Sachet, Q. Huo, L. G. Voigt-Martin, G. D. Stucky, F. Schuth, Science, 1996, 273, 768; Q. Huo, J. Feng, F. Schuth, G. D. Stucky, Chem. Mater., 1997, 9, 14; and L. Qi, J. Ma, H. Cheng, Z. Zhao, Chem. Mater., 1998, 10, 1623, the entire contents and disclosures of which are hereby incorporated by reference. In addition, polydisperse hollow micron-sized spheres were produced by interfacial synthesis in which tetraethyl orthosilicate (TEOS) was hydrolyzed with a base and subsequently neutralized with an acid, see C. E. Fowler, D. Khushalani, S. Mann, Chem. Commun., 2001, 2028, the entire contents and disclosure of which is hereby incorporated by reference. These methods typically involve a relatively long aging or stirring time, and lead to polydisperse particle populations that are sometimes aggregated.

EISA of aerosols is distinct from bulk solution synthetic methods in that all species are initially confined to droplets, which undergo evaporation-driven concentration changes as they pass through the process. The concentration changes produce self-assembled liquid-crystalline surfactant structures that template the organization of the inorganic precursor species (typically alkoxide-derived). Solidification of the inorganic network, for example by condensation reactions, followed by removal of the surfactant, leaves a mesoporous inorganic 'fossil' of the surfactant mesostructure. Porous submicron silica particles possessing a variety of different mesostructures have been previously reported based on EISA in submicron aerosols, see Y. Lu, H. Fan, A. Stump, T. L. Ward, T. Reiker, C. J. Brinker, Nature, 1999, 398, 223, the entire contents and disclosure of which is hereby incorporated by reference. The method has also been used to produce submicron nonporous polymer-silica composites, see H. Fan, F. van Swol, Y. Lu, C. J. Brinker, J. Non-Cryst. Solids, 2001, 285, 71, the entire contents and disclosure of which is hereby incorporated by reference. EISA of larger droplets in a spray dryer produced mesoporous silica particles with diameters in the tens of microns, but these particles were typically thin-walled hollow shells, and were often collapsed or fragmented, see P. J. Bruinsma, A. Y. Kim, J. Liu, S. Baskaran, Chem. Mater., 1997, 9, 2507, the entire contents and disclosure of which is hereby incorporated by reference. While the larger drops of a spray dryer potentially enable synthesis of larger mesoporous particles, the immediate high temperature environment may promote condensation reactions that solidify the silica structure before solvent evaporation is complete, leading to shell formation. In addition, the particle size distribution produced by spraying devices is broad. In the present invention, a method of droplet generation has been employed that produces monodisperse droplets, and a synthesis process that provides better control than may be provided with spray-based technology.

Figure 1A:
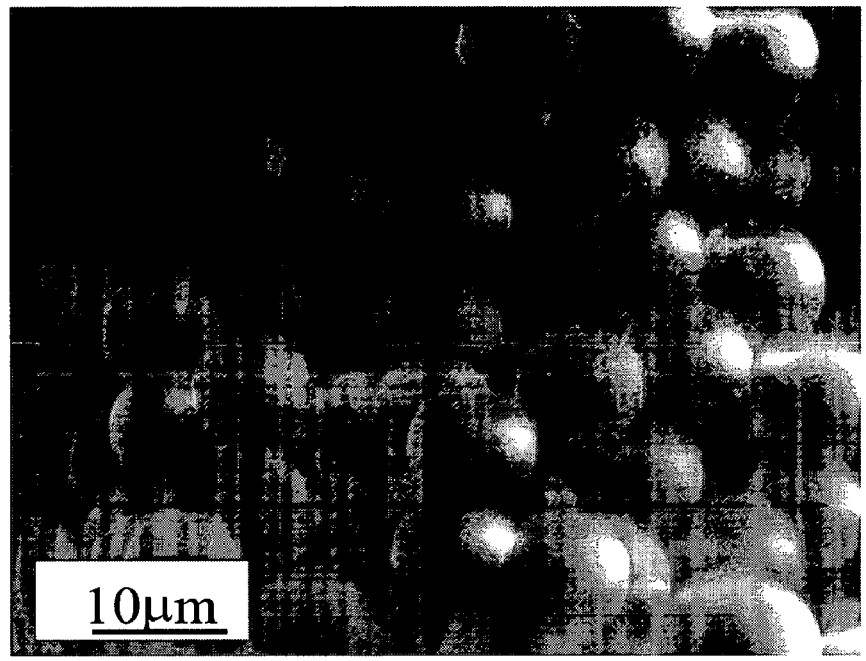
Figure 1B:
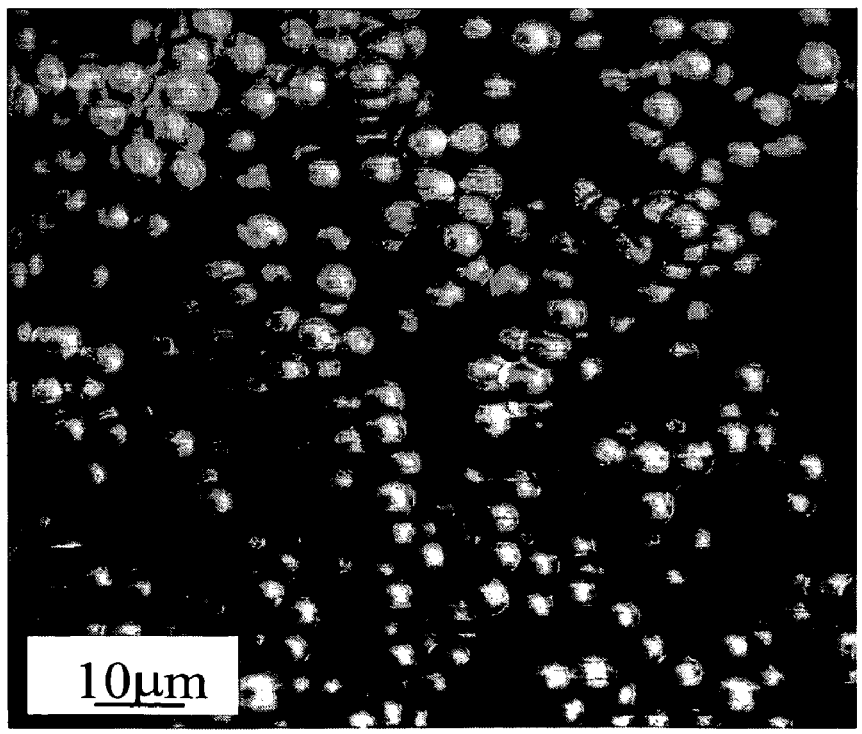

The cationic surfactant cetyltrimethyl ammonium bromide (CTAB), the non-ionic surfactant $CH_3(CH_2)_{15}$—$(OCH_2CH_2)_{20}$—OH (Brij-58), and the block copolymer ((ethylene oxide)$_{106}$(propylene oxide)$_{70}$(ethylene oxide)$_{106}$) (F-127) were employed as exemplary surfactants in the present invention. Two different silica precursor sols were employed: a pre-hydrolyzed acidic TEOS-based sol, referred to as A2, and an acidic aqueous TEOS solution. Particle size may be controlled by varying the orifice diameter and/or frequency in the VOAG or by varying the concentration of the precursor solution. Scanning electron micrographs of spherical porous silica particles (FIGS. 1A and 1B) illustrate that the particles are spherical, monodisperse in size, and possess a smooth surface morphology. The average particle size obtained using the A2 sol formulation with CTAB surfactant and a 20 μm orifice was 9.9±0.5 μm (mean and standard deviation of over 100 particles measured from SEM images) (FIG. 1A). The pH of the A2** formulation minimizes the siloxane condensation rate, thereby facilitating silica-surfactant self-assembly during aerosol processing, see C. J. Brinker, R. Sehgal, N. Raman, P. Schunk, T. Headley, J. Sol-Gel Sci. Technol., 1994, 2, 469, the entire contents and disclosure of which is hereby incorporated by reference. Using the same sol formulation with Brij-58 surfactant, a 10 μm orifice resulted in an average particle size of 6.0 μm±0.3 μm (FIG. 1B).

Figure 2:
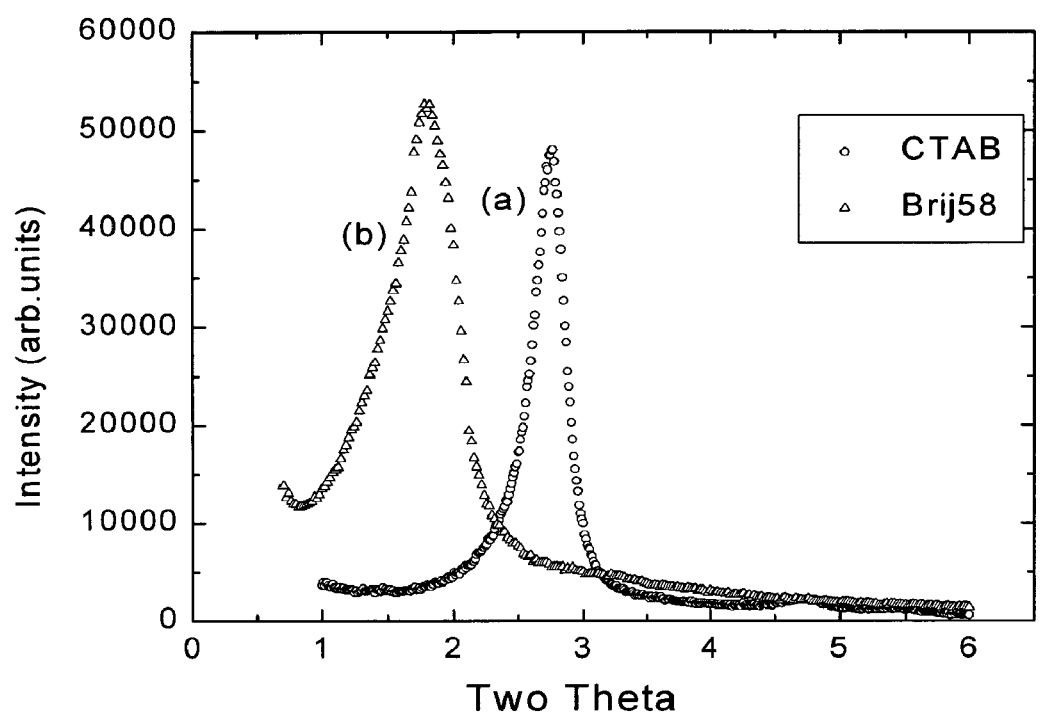
Figure 3A:
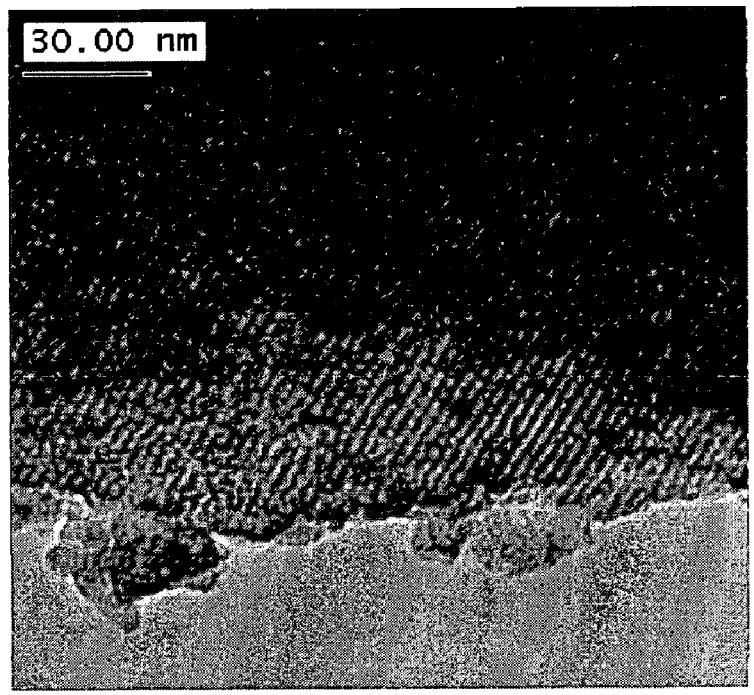
Figure 3B:
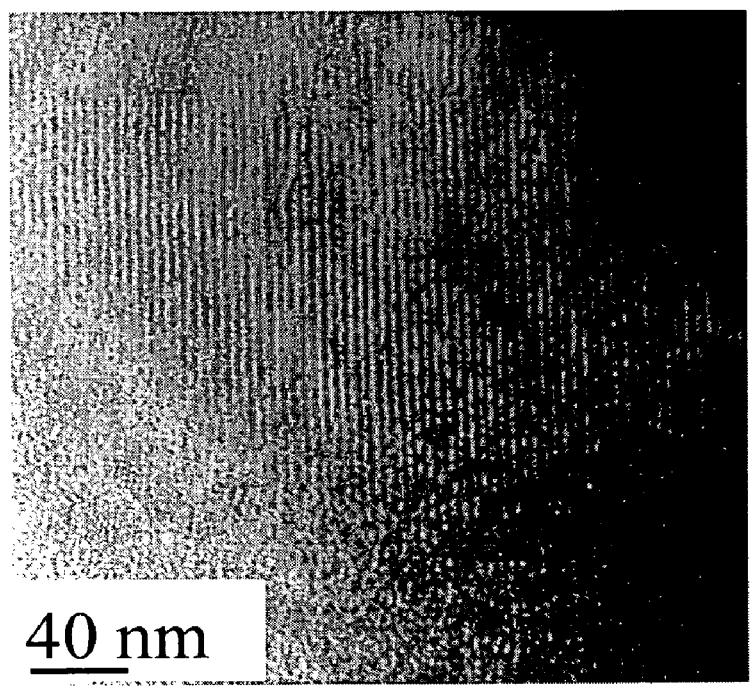

Powder X-ray diffraction (XRD) of particles corresponding to those shown in FIG. 1 revealed only a single peak (FIG. 2), indicating periodic short range structural order with d-spacings of 3.2 and 4.9 nm for particles produced with CTAB and Brij-58, respectively. The absence of higher order Bragg peaks indicates that these particles lack the high degree of long-range structural order that is commonly seen for a conventionally prepared mesoporous material. Transmission electron microscopy (TEM) images obtained from cross-sections of ultra-microtomed particle slices revealed that the particles produced from both CTAB and Brij-58 were not hollow. Particles produced with CTAB displayed a highly uniform periodic pore structure characteristic of 2-dimensional hexagonal order in many regions of the particles (FIG. 3A). Particles produced using Brij-58 displayed a similar uniform periodic pore structure in some regions of the particles (FIG. 3B); however, other regions displayed disordered mesostructure. Nitrogen adsorption-desorption isotherms showed typical features for mesoporous materials. The average (hydraulic) pore diameter ($d_p$) determined from nitrogen adsorption data (calculated as $d_p=4V_p/S_p$, where $V_p$ is total pore volume and $S_p$ is the BET (Brunauer, Emmett and Teller) surface area) was 1.8 and 2.8 nm for CTAB and Brij-58 templated powders, respectively. The corresponding BET surface areas of the particles were 908 and 516 $m^2/g$ for CTAB and Brij-58, respectively. These specific surface areas are consistent with previous results obtained using CTAB and Brij-56 surfactant, see Y. Lu, H. Fan, A. Stump, T. L. Ward, T. Reiker, C. J. Brinker, Nature, 1999, 398, 223, the entire contents and disclosure of which is hereby incorporated by reference.

Figure 4A:
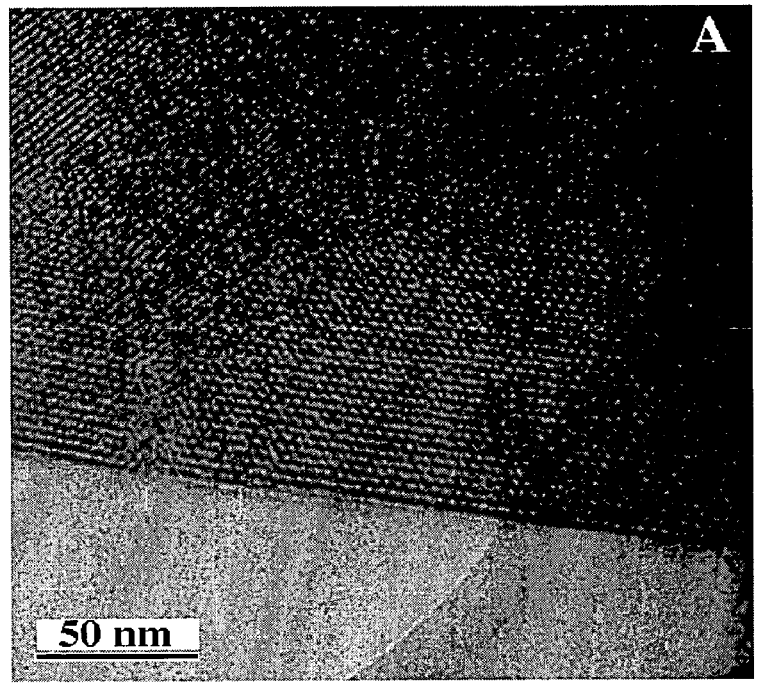
Figure 4B:
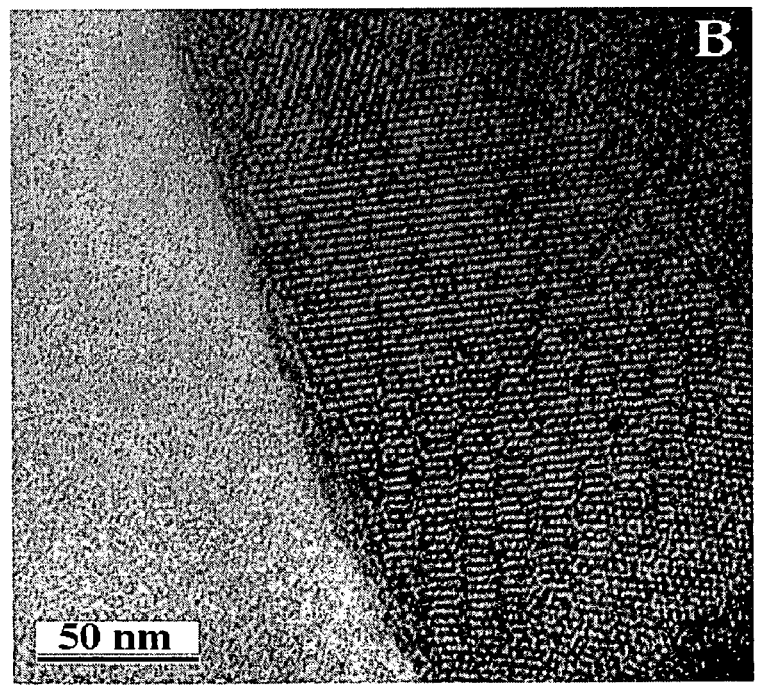

Particles produced using the aqueous TEOS precursor solution with CTAB surfactant displayed ordering that was comparable to those made with the A2** sol. FIGS. 4A and 4B show TEM images of an ultra-microtomed section of one of these particles. At low magnification, it was apparent that the particles were not hollow, while higher magnification revealed that pores were present in well-ordered domains across the entire cross section of the particles. In some regions, the TEM images appeared consistent with the hexagonally-packed tubular pore bundles that have been observed with the same solution and surfactant in submicron particles, while other areas were ordered but with a different (currently unidentified) mesophase In some areas near the surface, pores apparently are oriented parallel to the surface (FIG. 4A), which is consistent with what was observed in submicron particles. However, in other regions, the pore channels are apparently aligned perpendicular to the surface (FIG. 4A). Perpendicular pore alignment at the particle surface is of interest because alignment of tubular pore channels normal to the surface is optimal for unimpeded access to the pore interiors.

The present invention may also be extended to larger monodisperse droplets produced using a vibrating orifice aerosol generator (VOAG), see Venkata Rama Rao Goparaju, G. P. Lopez, J. Bravo, H. Pham, A. K. Datye, H. F. Xu, and T. L. Ward, Adv. Mater., 14 (18), 1301 (2002); and T. Buranda, J. Huang, Venkata Rama Rao Goparaju, L. K. Ista, R. S. Larson, T. L. Ward, L. A. Sklar, and G. P. Lopez, Langmuir 19 (5), 1654-1663 (2003), the entire contents and disclosures of which are hereby incorporated by reference. The monodisperse mesoporous particles produced by the present invention may range in size from several μm to roughly 10-50 μm. Because of the appropriate size and monodispersity, the present invention has shown that these particles may be surface modified with lipid bilayers and utilized as cell mimics, with fluorescence measured by flow cytometry methods commonly used for biological cells, see T. Buranda, J. Huang, Venkata Rama Rao Goparaju, L. K. Ista, R. S. Larson, T. L. Ward, L. A. Sklar, and G. P. Lopez, Langmuir 19 (5), 1654-1663 (2003), the entire contents and disclosure of which is hereby incorporated by reference. Monodispersity also facilitates the interpretation of diffusion rates from the particles, a property of interest for applications in delivery and controlled release.

Figure 5A:
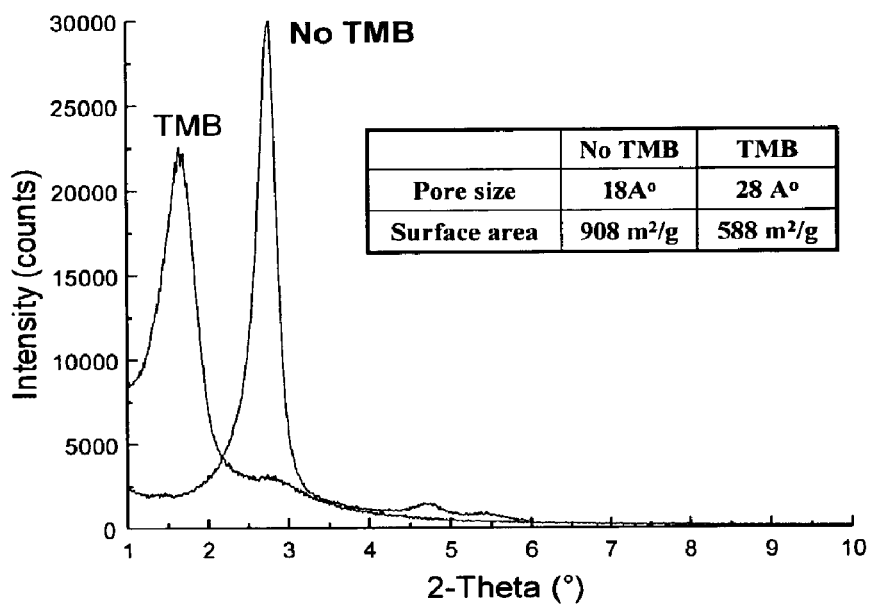

The present invention also provides for the use of trimethylbenzene (TMB) as a swelling agent. XRD shows that the hexagonal mesostructure in CTAB-templated particles is maintained with TMB addition up to levels of approximately 1 mol TMB:1 mol TEOS when used with the VOAG 10 μm orifice. At higher levels of TMB, the ordered mesostructure was lost, while at lower levels the degree of swelling was less. For TMB:TEOS=1:1, a substantial increase in the XRD d-spacing of the hexagonally ordered material was observed, accompanied by an increase in the mean pore diameter from 1.8 nm to 2.8 nm and a decrease in BET surface area from 908 $m^2/g$ to 588 $m^2/g$ (FIG. 5A). This indicates that, under these conditions, TMB is preferentially partitioned to the interior (hydrophobic portion) of the CTAB micellar structures.

Figure 5B:
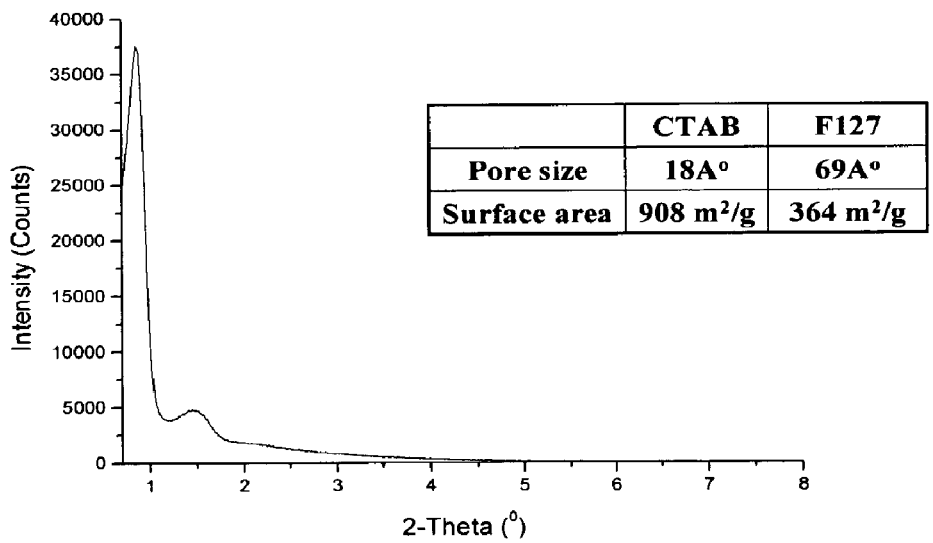

Pore size, as well as the type of mesostructure, may also be varied by the type of amphiphile. It is well known that the geometry and size of the amphiphilic molecule impact the type of stable mesostructures that are formed. In a particular embodiment, the present invention utilizes the nonionic surfactant Brij-58 with A2** to obtain hexagonally ordered mesoporous silica particles, with a BET surface area of 516 $m^2/g$ and mean pore diameter of 2.8 nm. Using the cationic surfactant CTAB, hexagonally ordered mesoporous particles were obtained with a pore diameter of 1.8 nm and a surface area of 908 $m^2/g$. Using the block copolymer F127 as an amphiphile, a much larger molecule than CTAB or Brij-58, the present invention obtained hexagonally-ordered mesoporous particles possessing a much larger mean pore diameter of 6.9 nm, and surface area of 364 $m^2/g$. XRD for the F-127 templated particles was consistent with weak hexagonal ordering (FIG. 5B), and SEM of a fractured particle (FIG. 7) clearly shows parallel pore channels consistent with 2-D hexagonal structure. It is notable that the SEM shows pore channels terminating perpendicular to the particle surface. This is quite interesting, since most of the TEM evidence in smaller submicron particles has indicated that hexagonally ordered pore channels were typically parallel to the surface, see M. T. Bore, S. B. Rathod, T. L. Ward, and A. K. Datye, Langmuir, 19 (2), 256-264 (2003), the entire contents and disclosure of which is hereby incorporated by reference. It is clear from the high measured surface areas in these particles that internal pore volume is accessible to $N_2$. However, this is the first direct evidence that some pores, at least, are open directly to the surface. This is a desirable attribute for applications involving transport in or out of the particles.

The addition of TMB at a level of approximately 1 mol TMB:1 mol TEOS, when used with a larger initial droplet diameter (VOAG 20 µm diameter orifice), led to particles possessing a body-centered cubic mesophase (FIG. 6). These particles possessed a mean pore diameter of 2.2 nm and surface area of 703 $m^2/g$, compared to a mean pore diameter of 2.8 nm and 588 $m^2/g$ for hexagonally-ordered particles produced using the same precursor solution with a 10 µm diameter orifice. This indicates that TMB does not function as a swelling agent in this case. Rather, TMB, in conjunction with the longer evaporation time of the larger initial droplets, functions as a phase modifying agent and facilitates the formation of a new more complex phase. These results reveal the importance of evaporation dynamics in this invention and potential complexity of mesophase behavior, and exemplify the rich variety of products that may arise due to complex mesophase behavior. Cubic phases have advantages for some applications due to the three-dimensionally connected pore network that ensures pore access at surfaces and uniform internal diffusion.

Diffusion rates into and out of the particles of the present invention are of interest for applications that may be related to, for example, controlled release or sensing schemes where the particle may provide a reservoir for a sensing agent. Transport rates of selected probe molecules have been examined by several different methods. FIG. 8 shows data for the uptake of probe molecules hexyl and decyl pyridinium chloride into mesoporous F127 templated silica particles. Data are based on periodic measurement of UV absorbance of the solution after centrifugation of particles. The initial concentration of solution for both fluorophores was 0.1 mM. Based on knowledge of the total pore volume for the F127-derived particles, the total uptake that may be expected based on simple infiltration of the particle pores is approximately $6\times10^{-8}$ mol/g. The levels of uptake displayed on FIG. 7 are probably explained by surface adsorption. The uptake rates and saturation capacity levels are different for the two different sized molecules. The diffusion of fluorophores rhodamine and fluorescein out of mesoporous particles produced by the methods of this invention have also been measured, indicating that a variety of molecule and ion types and sizes may be transported into and out of the particle pores.

In summary, the present invention provides for evaporation induced self-assembly (EISA) within microdroplets produced by a vibrating orifice aerosol generator (VOAG) for the production of monodisperse mesoporous silica particles. The process of the present invention exploits the concentration of evaporating droplets to induce the organization of various amphiphilic molecules, effectively partitioning the silica precursor (TEOS) to the hydrophilic regions of the structure. Promotion of silica condensation, followed by removal of the surfactant, provides ordered spherical mesoporous particles. Using a VOAG, the present invention produces highly monodisperse particles in the 3 to 10 µm diameter range, although particles may be produced having diameters as large as 50 µm. The cationic surfactant CTAB typically leads to a hexagonal mesostructure with mean pore size of about 2 nm and specific surface area around 900 $m^2/g$. The present invention has also shown that the pore size in CTAB-templated particles may be increased to 2.8 nm or more by incorporating trimethylbenzene (TMB) as a swelling agent. Under appropriate conditions, TMB preferentially locates inside and swells the hydrophobic regions of the surfactant mesostructure. TMB used in conjunction with larger initial droplet sizes results in modified phase behavior rather than swelling, producing particles with a cubic mesostructure and mean pore size of approximately 2.2 nm. Pore size may also be varied by the choice of amphiphile. Hexagonally ordered particles have been produced using the nonionic surfactant Brij-58 and block copolymer F127. These powders possessed a mean pore size of 2.8 nm and 6.9 nm, respectively. The uptake of alkyl pyridinium chloride molecules have recently been measured, revealing an uptake capacity that may be explained by surface adsorption (as opposed to simple pore infiltration).

The present invention has several significant advantages over the traditional solution-based self-assembly. The aerosol process is a continuous, scaleable process in which the entire particle synthesis process occurs on a time scale of several seconds or less. Highly spherical unaggregated particles are consistently produced under appropriate conditions. Finally, any additives, dopants or additional components that may be aerosolized from a solution or dispersion are inevitably incorporated into each particle. These features make the method attractive for producing microspheres to be used in, for example, sensor applications, where environmentally-sensitive fluorescent dyes may be incorporated into particles, see K. J. Albert, N. S. Lewis, C. L. Schauer, G. A. Sotzing, S. E. Stitzel, T. P. Vaid, D. R. Walt, Chem. Rev., 2000, 100, 2595; K. J. Albert, D. R. Walt, Anal. Chem., 2000, 72, 1947; and Y. Lu, L. Hang, C. J. Brinker, T. M. Niemczyk, G. P. Lopez, Sens. Actuators B, 1996, 35, 1, the entire contents and disclosures of which are hereby incorporated by reference. Similarly, porous interiors may serve as reservoirs for pharmaceutical agents in controlled release schemes. Mesoporous silica microspheres in the size range produced here are also highly promising as supports for biomolecules and biomembranes, which is an interesting new strategy for developing molecular affinity surfaces, biosensor devices and high-throughput screening devices, see A. Loidl-Stahlhofen, J. Schmitt, J. Noller, T. Hartmannn, H. Brodowsky, W. Schmitt, J. Keldenich, Adv. Mater., 2001, 13, 1829; and J. P. Nolan, S. Lauer, E. R. Prossnitz, L. A. Sklar, Drug Discov. Today, 1999, 4, 173, the entire contents and disclosures of which are hereby incorporated by reference. A number of other possible applications may be envisioned, such as optical materials, catalyst supports, biocompatible microreactors and molecular separations media, see J. D. Joannopoulos, P. R. Villeneuve, S. Fan, Nature, 1997, 386, 143; K. K. Unger, D. Kumar, M. Grun, G. Buchel, S. Ludtke, T. Adam, K. Schumacher, S. Renker, J. Chrom. A, 2000, 892, 47; B. J. Scott, G. Wirnsberger, G. D. Stucky, Chem. Mater., 2001, 12, 3140; A. Corma, Chem. Rev., 1997, 97, 2373; and K. Tsumoto, S. M. Nomura, Y. Nakatani, K. Yoshikawa, Langmuir, 2001, 17, 7225, the entire contents and disclosures of which are hereby incorporated by reference.

The convenient control of particle size and monodispersity demonstrated in the present invention are important complements to the control of internal mesostructure and pore size provided by surfactant templating.

Example I

Two precursor solution formulations were used: one based on an acidic silica sol (A2), and one based on an aqueous TEOS solution. For the A2 formulation, the solutions were synthesized by addition of CTAB: $CH_3(CH_2)_{15}N^+(CH_3)_3Br^-$ (Aldrich), Brij-58: $CH_3(CH_2)_{15}-(OCH_2CH_2)_{20}-OH$ (Aldrich) to an acidic silica sol (A2**), as reported in Y. Lu, H. Fan, A. Stump, T. L. Ward, T. Reiker, C. J. Brinker, Nature, 1999, 398, 223, the entire contents and disclosure of which is hereby incorporated by reference, or Pluronic block copolymer F127 ((ethylene oxide)$_{106}$(propylene oxide)$_{70}$(ethylene oxide)$_{106}$). In a typical preparation, tetraethylorthosilicate (TEOS) (Aldrich), ethanol, deionized water (conductivity less than 18.2 MΩ-cm) and dilute HCl (mole ratios 1:3.8:1:0.0005) were refluxed at 60° C. for 90 minutes to provide the stock sol. Then, 10 mL of stock sol was diluted with ethanol, followed by addition of water, dilute HCl, and aqueous surfactant solution (1.5 grams of surfactant dissolved in 20 ml of water) to provide final overall TEOS:ethanol:$H_2O$:HCl:surfactant molar ratios of 1:27:55:0.0053:0.19 and 1:22:55:0.0053:0.06 for CTAB and Brij-58 sols, respectively. For the aqueous TEOS-CTAB precursor solution, CTAB was mixed with water (5 wt % CTAB) and stirred to obtain a clear solution. To this solution, TEOS and 1N HCl were added to give a solution in which the final molar ratio of TEOS:$H_2O$:CTAB:HCl is 1:63.28:0.15:0.0227. This sol was stirred for about 10 minutes before beginning a powder synthesis run.

The monodisperse droplets were generated by means of a VOAG (TSI Model 3450). In the VOAG, the aerosol solution was forced through a small orifice (10 μm or 20 μm) by a syringe pump, with syringe velocities of approximately $2\times10^{-4}$ cm/s (~$1.4\times10^{-3}$ cm$^3$/s) and $8\times10^{-4}$ cm/s (~$4.7\times10^{-3}$ cm$^3$/s) for the 10 μm and 20 μm orifices, respectively. This delivery rate was adjusted to provide a stable operating pressure of 340-420 kPa. The liquid stream was broken up into uniform droplets by the vibrating orifice. The frequency range employed was 40-200 kHz, with the final setting adjusted to eliminate satellite droplets. The droplets were then injected axially along the center of a turbulent air jet to disperse the droplets and to prevent coagulation. Following the mixing of the dispersed droplets with a much larger volume of filtered dry air, the droplet-laden gas stream flowed through a 2.5 cm diameter quartz tube into a three-zone furnace (0.9 m heated length) maintained at 500° C. (A2 runs) or 420° C. (TEOS solution runs). This provided a mean residence time of approximately 0.3 second in the heated zone. The particles were collected on a filter maintained at approximately 80° C. by a heating tape. Collected particles were calcined in air at 400-450° C. for 4 hours (A2 runs) or at 500° C. for 12 hours (TEOS solution runs) to remove the surfactant template. The typical powder production rate using the VOAG was 0.35 g $SiO_2$/h.

The particles were characterized by scanning electron microscope (Hitachi S-800) and X-ray diffraction (Siemens D5000, CuK$_\alpha$ radiation, λ=1.5418 Å) techniques. Surface area and pore size distribution studies were carried out by nitrogen adsorption/desorption at 77K using a Micromeritics ASAP 2000 porosimeter. For cross-sectional TEM (JEOL 2010, 200 KV), particles were embedded in an epoxy and then cross-sectioned using a Sorvall MT-5000 Ultra Microtome machine. Surface area values were derived from the BET (Brunauer-Emmett-Teller) theory, and mean pore diameters were based on the BJH (Barrett-Joyner-Halenda) theory (adsorption branch) or calculated from total pore volume and BET surface area ($4V_p/S_p$, where $V_p$ is total pore volume and $S_p$ is BET surface area).

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of producing monodisperse non-hollow mesoporous silica spheres having a diameter of greater than or equal to about 3 μm and less than or equal to about 50 μm comprising:
    combining a precursor aqueous or alcohol based solution comprising tetraethylorthosilicate with an amphiphile to form a sol;
    creating monodisperse droplets of said sol using a vibrating orifice aerosol generator,
    mixing a volume of the monodisperse droplets with a volume of dry air, wherein the volume of dry air is larger than the volume of monodisperse droplets;
    evaporating solvent from said monodisperse droplets of said sol to induce self-assembly of said amphiphile in said monodisperse spheres;
    heating to promote condensation of said tetraethylorthosilicate to produce said silica; and
    removal of said amphiphile by thermal or chemical means; to produce a monodisperse population of non-hollow mesoporous silica spheres having a diameter of greater than or equal to about 3 μm and less than or equal to about 50 μm.

2. The method of claim 1, wherein said amphiphile comprises a surfactant.

3. The method of claim 2, wherein said surfactant comprises cetyl trimethyl ammonium bromide.

4. The method of claim 2, wherein said surfactant comprises Brij-58.

5. The method of claim 1, wherein said amphiphile comprises a block copolymer.

6. The method of claim 5, wherein said block copolymer comprises (ethylene oxide)$_{106}$(propylene oxide)$_{70}$(ethylene oxide)$_{106}$.

7. The method of claim 1, wherein said monodisperse mesoporous silica spheres have a diameter between about 3 and about 10 μm.

8. The method of claim 1, wherein said monosdisperse mesoporous silica spheres have at least one pore has having a diameter between about 2 and about 10 nm.

9. The method of claim 1, wherein said tetraethylorthosilicate comprises a pre-hydrolyzed acidic tetraethylorthosilicate.

10. The method of claim 1, wherein said tetraethylorthosilicate comprises an acidic aqueous tetraethylorthosilicate.

11. The method of claim 1, wherein said vibrating orifice aerosol generator comprises an orifice with a diameter from about 10 μm to about 100 μm.

12. The method of claim 1, wherein said monodisperse mesoporous silica spheres comprise a plurality of pores.

13. The method of claim 12, wherein said plurality of pores comprise hexagonally-packed tubular pore bundles.

14. The method of claim 12, wherein near the surface of said monodisperse mesoporous silica spheres, said pores are oriented parallel to said surface.

15. The method of claim 12, wherein near the surface of said monodisperse mesoporous silica spheres, said pores are oriented perpendicular to said surface.

16. The method of claim 1, wherein said sol further comprises a swelling agent.

17. The method of claim 16, wherein said swelling agent comprises trimethylbenzene.

18. The method of claim 17, wherein said trimethylbenzene and said tetraethylorthosilicate are in a ratio of about 1:1 mol.

19. The method of claim 1, wherein said sol further comprises an organic additive that influences mesophase behavior.

20. The method of claim 19, wherein said organic agent comprises trimethylbenzene.

21. The method of claim 20, wherein said trimethylbenzene and said tetraethylorthosilicate are in a ratio of about 1:1 mol.

22. The method of claim 1 wherein the spheres in the monodisperse population of non-hollow mesoporous silica spheres are unaggregated.

23. The method of claim 1 wherein the monodisperse non-hollow mesoporous silica spheres have a diameter equal to or greater than about 10 μm and equal to or less than about 50 μm.

* * * * *